US00RE44312E

(19) United States
(12) Reissued Patent
Vieira

(10) Patent Number: US RE44,312 E
(45) **Date of Reissued Patent: *Jun. 25, 2013**

(54) EVAPORATION DEVICE FOR MULTIPLE VOLATILE SUBSTANCES

(76) Inventor: Pedro Queiroz Vieira, Cascais (PT)

( * ) Notice: This patent is subject to a terminal disclaimer.

(21) Appl. No.: 11/655,036

(22) Filed: Jan. 18, 2007

Related U.S. Patent Documents

Reissue of:

(64) Patent No.: 6,563,091
Issued: May 13, 2003
Appl. No.: 09/918,898
Filed: Jul. 31, 2001

U.S. Applications:

(63) Continuation of application No. 11/123,252, filed on May 5, 2005, now Pat. No. Re. 40,464.

(30) Foreign Application Priority Data

Apr. 5, 2001 (EP) ..... 01107795

(51) Int. Cl.
*H05B 3/02* (2006.01)
*F24F 6/08* (2006.01)

(52) U.S. Cl.
USPC ..... 219/486; 392/395

(58) Field of Classification Search
USPC ..... 219/483–508, 543–548; 392/386–395; 261/139–142, 94, 95, 104, DIG. 65
See application file for complete search history.

(56) References Cited

U.S. PATENT DOCUMENTS

| | | | | |
|---|---|---|---|---|
| 1,154,113 | A | 9/1915 | Hadaway, Jr. | |
| 1,346,793 | A | 7/1920 | Bunnell et al. | |
| 2,715,056 | A | 8/1955 | Wilson | |
| 3,028,100 | A | 4/1962 | Xenakis et al. | |
| 3,414,864 | A * | 12/1968 | Barrington | 338/300 |

(Continued)

FOREIGN PATENT DOCUMENTS

| | | | |
|---|---|---|---|
| EP | 0 362 397 | A1 | 4/1990 |
| EP | 0 451 331 | A1 | 10/1991 |

(Continued)

OTHER PUBLICATIONS

"Defendant Dial Corporation's Answer, Defenses and Counterclaims in Response to Plaintiffs' Complaint," filed Jan. 16, 2008, in *S. C. Johnson & Son, Inc., and Consultoria Técnica e Representações, LDA* vs. *The Dial Corporation,* Case No. 07-C-0689-C.

(Continued)

*Primary Examiner* — Sang Paik
(74) *Attorney, Agent, or Firm* — Cort Flint

(57) ABSTRACT

An evaporation device is disclosed for evaporating volatile substances such as insecticides and aromatics of a type having a housing containing a heating block with a heating element, a container for a volatile substance to be evaporated, a wick having a wick end protruding out of the container into a wick opening in the heating block, a switching device for the activation and deactivation of the heating device, and an adjusting device for the adjustment of the degree of evaporation. Preferably, two heating elements with different heating capacity are carried by the heating block. The heating elements are operatively connected to the switching device to adjust the heat output of the heating device and the degree of evaporation of the volatile substance.

26 Claims, 5 Drawing Sheets

U.S. PATENT DOCUMENTS

| | | | | | |
|---|---|---|---|---|---|
| 3,440,589 | A | | 4/1969 | Minks | |
| 3,633,881 | A | | 1/1972 | Yurdin | |
| 3,672,568 | A | | 6/1972 | Foote | |
| 4,498,071 | A | | 2/1985 | Plough et al. | |
| 4,621,768 | A | | 11/1986 | Lhoste et al. | |
| 4,629,604 | A | | 12/1986 | Spector | |
| 4,659,905 | A | * | 4/1987 | Gabrosek et al. | 219/212 |
| 4,739,928 | A | | 4/1988 | O'Neil | |
| 4,742,960 | A | | 5/1988 | Bustillo et al. | |
| 5,038,394 | A | | 8/1991 | Hasegawa et al. | |
| 5,175,791 | A | * | 12/1992 | Muderlak et al. | 392/390 |
| 5,222,186 | A | * | 6/1993 | Schimanski et al. | 392/395 |
| 5,264,681 | A | | 11/1993 | Nozaki et al. | |
| 5,427,278 | A | | 6/1995 | Gardner, III | |
| 5,438,914 | A | | 8/1995 | Hohn et al. | |
| 5,647,053 | A | | 7/1997 | Schroeder et al. | |
| 5,725,152 | A | | 3/1998 | Akyu | |
| 6,078,728 | A | | 6/2000 | O'Rourke et al. | |
| 6,172,343 | B1 | | 1/2001 | Nothe et al. | |
| 6,236,807 | B1 | | 5/2001 | Ruffolo et al. | |
| 6,278,840 | B1 | | 8/2001 | Basaganas Millan | |
| 6,361,752 | B1 | | 3/2002 | Demarest et al. | |
| 6,446,583 | B2 | | 9/2002 | Vieira | |
| 6,466,739 | B2 | | 10/2002 | Ambrosi et al. | |
| 6,487,367 | B2 | | 11/2002 | Vieira | |
| 6,501,906 | B2 | | 12/2002 | Vieira | |
| 6,896,196 | B2 | | 5/2005 | Vieira | |
| RE40,464 | E | * | 8/2008 | Vieira | 219/486 |

FOREIGN PATENT DOCUMENTS

| | | | | |
|---|---|---|---|---|
| EP | 0 591 537 | A1 | | 4/1994 |
| EP | 0 911 041 | | * | 4/1997 |
| EP | 0 911 041 | A2 | | 4/1999 |
| EP | 0 943 344 | A1 | | 9/1999 |
| EP | 943 344 | | | 9/1999 |
| EP | 0 962 132 | A1 | | 12/1999 |
| EP | 962 132 | | | 12/1999 |
| EP | 0 998 947 | A1 | | 5/2000 |
| EP | 1 055 430 | | | 11/2000 |
| FR | 2 804 662 | | | 8/2001 |
| GB | 2 279 010 | | | 12/1994 |
| JP | 58135183 | | | 8/1983 |
| JP | 64-39745 | | | 3/1989 |
| JP | 3-147731 | | | 6/1991 |
| JP | 11-000391 | | | 1/1999 |
| WO | WO 97/39779 | | | 10/1997 |
| WO | WO 98/19526 | | | 5/1998 |
| WO | WO 98/58692 | | | 12/1998 |
| WO | WO 01/05442 | | | 1/2001 |

OTHER PUBLICATIONS

"The Dial Corporation's Original Answers to Plaintiffs' First Set of Interrogatories," filed Feb. 19, 2008, in *S. C. Johnson & Son, Inc., and Consultoria Técnica e Representações, LDA* vs. *The Dial Corporation,* Case No. 07-C-0689-C.

"The Dial Corporation's First Supplemental Answers to Plaintiffs' Interrogatory Nos. 7 and 8," filed Mar. 3, 2008, in *S. C. Johnson & Son, Inc., and Consultoria Técnica e Representações, LDA* vs. *The Dial Corporation,* Case No. 07-C-0689-C.

Office Action in U.S. Appl. No. 11/123,252 dated May 24, 2006.

Office Action in U.S. Appl. No. 11/123,252 dated Sep. 26, 2007.

* cited by examiner

EVAPORATION DEVICE FOR MULTIPLE VOLATILE SUBSTANCES

Matter enclosed in heavy brackets [ ] appears in the original patent but forms no part of this reissue specification; matter printed in italics indicates the additions made by reissue.

*CROSS REFERENCE TO RELATED APPLICATIONS*

*This application is a continuation of U.S. application Ser. No. 11/123,252 filed May 5, 2005, now Reissue Pat. No. 40,464. The present application, U.S. application Ser. No. 12/214,223, now abandoned, U.S. application Ser. No. 12/592,151, now abandoned, and Reissue Pat. No. 40,464 are all reissues of U.S. Pat. No. 6,563,091.*

BACKGROUND OF THE INVENTION

*More than one reissue has been filed in connection with this patent. Specifically, the application that resulted in this reissue claims priority to Reissue Pat. No. 40,464, and also is a parent application to reissue application Ser. No. 12/592,151, filed Nov. 19, 2009.*

The present invention relates to a device for evaporating volatile substances, in particular insecticides and/or aromatics.

Insecticide and aromatic evaporation devices are generally known. For example, evaporation devices are known where a small plate, introduced into an evaporation device and impregnated with an active ingredient, is heated in order to evaporate the active ingredient. Furthermore a method is also known by which a container containing a volatile substance is introduced into a housing of an evaporation device. This container comprises a wick that conveys the substance to be evaporated by means of capillary action out of the container, whereby the wick end protruding from the container is located next to a heating element such as a ceramic block The substance is evaporated through the heat radiated by the ceramic block and can escape from the housing into the environment through aeration slits in the housing.

A disadvantage with prior evaporation devices is that it was not possible to adapt the degree of evaporation to the prevailing room conditions or to the different sensitivities of persons present in the room. Thus, for example, in smaller rooms with insufficient air ventilation, it is desirable to lower the degree of evaporation, which was not possible with prior evaporation devices. Furthermore, it is especially desirable to be able to adjust,the evaporation for insecticides, so that the degree of evaporation can be adjusted in accordance with the sensitivity of persons present in the room. This has also not been possible with the prior evaporation devices.

The ability to adjust the degree of evaporation for volatile substances is now known in the prior art. For example, EP 0 962 132 A1 discloses a device for the evaporation of volatile substances, in particular for insecticides and/or aromatics, by using a housing with a heating device located therein that comprises a ceramic heating block. The heating block uses a heating element to heat the heating block and evaporate a volatile substance. A container is carried in the housing and stores a volatile substance to be evaporated. A wick is inserted into the container with a wick end protruding from the container into a wick opening formed in the heating block. The invention discloses a switching device for activating and deactivating the heating element, as well as an adjusting device for adjusting the degree of evaporation. The housing of the evaporation device contains a large opening for receiving the container holder. On the outside of the container holder is a cylindrical extension with a helicoidal thread projection that extends in the form of spiral around the cylindrical extension. The thread projection interacts with a threaded bushing, already inside the housing, which has a receiving opening for the cylindrical extension of the container holder, and a corresponding counter-element to the tread projection on an inner side of this receiving opening. The bushing is moved by means of a pivoting lever to the outside of the housing. The container with a volatile substance to be evaporated is inserted into the container holder, with the wick extending into the wick opening in the form of a depression at the edge of the heating block above the container holder. To adjust the degree of evaporation, the bushing is rotated into a horizontal plane via the pivoting lever of the bushing. The interaction of counter-elements and thread projection make it possible for the container holder to be shifted in the longitudinal direction of the wick so that the wick end can be fixed in a different position relative to the heating block. This type of design, where the degree of evaporation is adjusted by changing the relative distance between the heating element and wick, is relatively expensive due to the number of complicated components required to effect the adjustments.

Another type of evaporation device is known from WO 98/19526, in which the heating output remains constant and the relative distance between the wick and the heating element is adjusted to control evaporation. The evaporation device comprises a housing into which a container with a wick can be screwed. The container is connected via a bushing to a swivel arm that moves in a guide slot, extending radially at an angle to the horizontal in the housing wall. Through the coupling of the swivel arm to the container, the container is lifted relative to the housing in the axial direction when the swivel arm is turned radially. As a result, the wick end protruding from the container may be shifted relative to the fixed heating element. On the whole, this is a relatively expensive and complicated construction with a great number of additional components, making the evaporating device expensive to manufacture.

It is also disclosed in EP 0 943 344 A1 that the relative distance between the heating element and wick can be changed to adjust the degree of evaporation while the heating output is maintained constant. The evaporation device includes a resistance heating element with a connecting plug that is threaded into a housing element where the container holding the substances to be evaporated is located. Pin openings are provided on the housing element into which locking pins are inserted in such manner that they mesh with the threads of the plug. The distance between the resistance-heating element and the wick end protruding from the container can be changed by twisting the plug element. The plug element can be mounted eccentrically in the housing element so that it too can be used to change the relative distance between the wick end and the resistance heating element to achieve the desired degree of evaporation. However, this method of adjusting the degree of evaporation is relatively complicated in construction and is also expensive to manufacture.

A similar design with the disadvantages discussed above is disclosed in WO 98/58692, wherein the task of changing the evaporation capacity is accomplished by changing the position of the wick relative to the heating block.

Moreover, it is a common feature among all these known evaporation devices that they are relatively large in size and therefore less attractive aesthetically. The large size in design of the prior art is caused by the number of adjustment components needed to control the degree of evaporation. This large size turn affect the overall visual impressions of a room, and even an outdoor area.

The types of evaporation device disclosed above can only evaporate one substance at a time and requires a changing of the volatile substance container to evaporated different insecticides or aromatics. Especially when used for aromatherapy, it is often necessary to evaporate two or more aromatics together. This would normally require a corresponding number of evaporation devices, depending on the number of aromatics to be mixed and evaporated. As well, all these prior art devices would require the utilization of several evaporation devices to use multiple insecticides simultaneously.

It is therefore an object of the invention to provide a single evaporation device for multiple volatile substances, in particular insecticides and/or aromatics, which is simple in structure and can be produced economically yet the degree of evaporation can be easily adjusted to meet current requirements

SUMMARY OF THE INVENTION

The above objective is accomplished according to the present invention by providing at least two heating elements with different heating capacities on a heating block. The heating elements are connected to a switching system that adjusts their activation and deactivation. Advantageously, with a design of this type, the desired degree of evaporation, commonly referred to as the evaporation capacity, can be adjusted through one single switching system. Depending on the number of heating elements in the heating block, the device can be made in a desirable small size. It is especially advantageous for the manufacturing cost, that the costly components needed to adjust the position of the wick relative to the heating element, are no longer needed. The degree of evaporation is not adjusted by changing the relative distance between wick and heating element, but by changing the heating capacity. This is accomplished by switching between the different heating elements.

For example, varying heating capacities from different heating elements can be used to regulate the evaporation of the substances, usually aromatics or insecticides, to cause a rapid or slow evaporation. Because the evaporation capacity can be easily adapted to the substance being evaporated, a great variety of multi-functional applications is possible from a single evaporation device. A design of this type represents a simple and economic alternative to the evaporation devices currently known from the state of the art, where the degree of evaporation can be changed only in an expensive and complicated manner by mechanical means that adjusts the distance between the volatile substances and heating element. In addition, the risk that the threads which adjust the distance of the container to the heating element may become locked by components of the substances to be evaporated, is avoided.

As a result, one simple single device for the evaporation of volatile substances is provided, in which simple and quick adaptation and change-over to the applicable aromatic or insecticide to be evaporated is now possible. Depending on the number of heating elements located in the heating block, all of these, or at least part of them, can have a different heating capacity so that the degree of evaporation is highly adjustable, depending on the number of activated heating elements. In the preferred embodiment, the heating elements for the adjustment of the degree of evaporation can be selectively activated or deactivated individually, or together in groups. As a result, the possibilities for application of the device are considerably increased so that an even better adaptation of the degree of evaporation to the substance to be evaporated is possible.

To achieve the compact design, the wick opening is formed approximately in the center of two heating elements. In the preferred embodiment, a switching device serves to either deactivate both heating elements. Depending on the desired evaporation capacity of the substance to be evaporated, either one or the other heating element can be switched on. In this sense, the switching device simultaneously acts as an adjustment device. If necessary, both heating elements can be activated jointly in one switch position for a more rapid evaporation.

In one preferred embodiment, the heating block has an approximately rectangular or approximately oval form, whereby the wick opening is formed approximately in the central area of the heating block between heating elements. This results in an especially well controlled and adjustable heat transmission in the direction of the wick opening on the heating block, allowing for optimal evaporation of the volatile substance. Ease of control and adjustability for different evaporation capacities of different heating elements is achieved when the heating elements are at the same distance from the wick opening with symmetrical placement of the heating elements relative to the wick openings.

In an alternative embodiment, at least two wick openings are provided on the heating block. Each heating element is assigned to at least one wick opening, which together constitutes one heating unit. With this design greater flexibility and functionality is achieved. By having a number of heating elements and corresponding wick openings, a plurality of individual heating units, each consisting of heating elements and wick openings, can be integrated into one single device. These individual heating units can be activated and deactivated together or separately via the switching system so that an individual inclusion or exclusion is possible, depending on the current evaporation demands.

Generally, one heating element can always be assigned to one wick opening. It is, however, also possible for more than one heating element with different heating capacities to be assigned to a single wick opening area. Thus, depending on the currently activated and assigned heating element, different evaporation capacities, e.g., rapid or slow, can be assigned to one wick opening area. If necessary, however, all the associated heating elements can be actuated together, or individual heating elements in a group can be activated alone or in pairs. In the same manner, it is also possible for one of several heating elements to be assigned to several wick openings so that, if necessary, several wick opening areas can be heated to evaporation temperature through one heating element. Overall, the evaporation capacity can be easily adapted to the current substance to be evaporated whereby the integration of multiple functions into a single component enables it to be used in a variety of applications. Furthermore, it is also possible with design to use identical heating elements, producing the same heating capacity, to evaporate different substances having about the same evaporation temperature.

In a preferred embodiment, two wick openings, as well as two heating elements, are provided on a heating block with one heating element assigned to each wick opening. There are different possibilities for the placement of the two wick openings and assigned heating units on the heating block. However, in order to be able to activate and deactivate the individual heating units separately from each other without causing one heating unit to heat up the area of the other heating unit, two wick openings must be located at a distance from each other in a central area between the two heating elements, preferably located at the edge of the heating block. With such an arrangement of heating elements be located a sufficient distance from each other, and, especially from the other wick opening, it is possible to prevent the transfer of heat in the area from one heating unit to the other. As a result, any undesired evaporation that might by caused from adjacent heating units is prevented.

The two volatile substance containers can be separate containers with one single wick. As an alternative, it is also possible to provide one single container with two chambers separated from each other, whereby different substances to be evaporated have separate wicks for each chamber. In the latter case, an especially compact design of the evaporation device is possible in actual application.

The thermal uncoupling of the different heating units is considerably reinforced when at least one separator is provided in an area between the two wick openings, creating at least partial uncoupling of the two heating units. This separator preferably consists of an air gap going through the heating block in the area between the two wick openings. Such thermal uncoupling by means of a separator, such as the air gap, is also possible in evaporation devices having more than two heating units.

A small-size and well-suited heating element with good heating capacity is created by using an electric resistance element contained in the heating block. The electrical resistance elements are approximately rod-shaped. Where two resistance elements are used with a central wick opening, the electrical resistance elements are placed approximately parallel to each other. This allows for an especially compact and efficient design of the heating device. In order to provide different heating capacities, resistance elements with different resistance values are used to form the heating elements. The heating element is connected via electric lines to a connection plug on the housing and to a switching device on the housing. The electric resistance element can consist of any know resistance elements, such as a PTC resistance. In the preferred embodiment, every electrical resistance element is provided with a rod-shaped resistance body covered with a resistance layer that is notched and/or machined off in spots to set a given resistance value adapted to the evaporation temperature for the composition of the applicable substance to be evaporated. This allows for the construction a heating device with small dimensions, creating an overall miniaturized device for the evaporation of volatile substances. Advantageously, a resistance element of the type described above for use in heating units can be of relatively small size so that the heating block and the entire housing containing the heating unit may be given a relatively small size. Thus, evaporation devices with small dimensions such as miniaturized evaporation device can be created, while at the same time using one or more suitably adapted low-volume containers in the housing. Thanks to the reduced expenditure on material and components, such a miniaturized evaporation device can be produced relatively simply and inexpensively as a disposable item.

It is an additional advantage of such an evaporation device that the evaporation temperature can be adjusted optimally to the composition of the substance to be evaporated at any time with a resistance element of this type, where the resistance layer for the setting of a given resistance value is cut or ground in at different locations. Thereby, the danger of flammability of the overall device is reduced and any possible negative effect on the degree of evaporation can be avoided. There are different possibilities for notching or grinding the resistance layer in order to set a given resistance value. In a preferred embodiment, the resistance layer is cut into and around the rod-shaped, cylindrical resistance body in a helicoidal form, by helicoidal laser cutting. With such a helicoidal cut the resistance value can be adjusted very precisely and easily for optimal evaporation performance. The resistance layer can in principle be also made of different materials in the form of a special metal layer. However, the resistance layer is preferably a metal oxide layer, such as nickel-chrome alloy burned on thermochemically by vacuum metallizing or cathodic sputtering in the form of a thin layer. After the resistance layer has been applied, it is preferably subjected to a thermal process in order to stabilize the resistance layer. The resistance body can be made of ceramic in this case, preferably with a high content of $AL_2O_3$ (aluminum oxide), so that an especially good heat conductivity of the resistance body, and thereby of the resistance element overall, is achieved. The context of $AL_2O_3$ depends on the actual installation conditions such as housing material, the wick material, etc., being used. Metal caps can be pressed on the ends of the coated, rod-shaped resistance body. Electrical lines are connected to each of these metal caps, preferable by welding, which are in turn then connected to the connection plug. Preferably, copper wire with good electrical conductivity is used for the electric lines. As a result, a good electrical contact with the resistance layer is easily and reliably achieved.

Several possibilities exist for the installation of the rod-shaped resistance element on the heating block. In an especially preferred embodiment, the rod-shaped resistance element can be inserted into a recess in the heating block, whereby the resistance element is encapsulated therein by a highly heat-conductive material in order to fix the resistance element in the heating block. The highly heat-conductive material is preferably a flame-resistant insulation cement. Furthermore, a slit is formed on either side of the resistance element, at the opposite ends of the recess, whereby the electrical lines come out of the heating block and go through these slits to the connection plug. With a design of this type, the resistance element can easily be inserted into the recess during assembly using a clamping lock, so that the resistance element cannot slip during the encapsulating process. In addition, the electrical lines can easily be curved in the direction of the connection plug. The electric lines can be insulated in a conventional manner. Additionally, the wick opening is preferably made in the form of a round passage opening in the heating block.

Depending on the application of the device, several possibilities for the design of the switching device are possible. When used with a compact, small-size device according to the invention, the switch can be integrated directly on the housing in the form of a manual switch. Alternatively, it is also possible to make the switching and/or control device in the form of a programmable microprocessor which is suitably connected to the device.

Especially simple and rapid assembly of the heating device in the housing is possible if the housing is made from two parts, an upper shell and a lower shell. The upper shell and the lower shell can be connected with each other by locking and/or clip elements. The lower shell preferably contains connecting members to connect the container to the housing locking elements. At least one of the two shells is provided with aeration slit for the escape of the evaporated substance into the environment. The aeration slits are preferably made in the area above the wick end in the upper shell. The production of a housing of this type in two parts is especially simple and inexpensive.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Referring now in more detail to the drawings, the invention will now be described in more detail.

Figure 1:
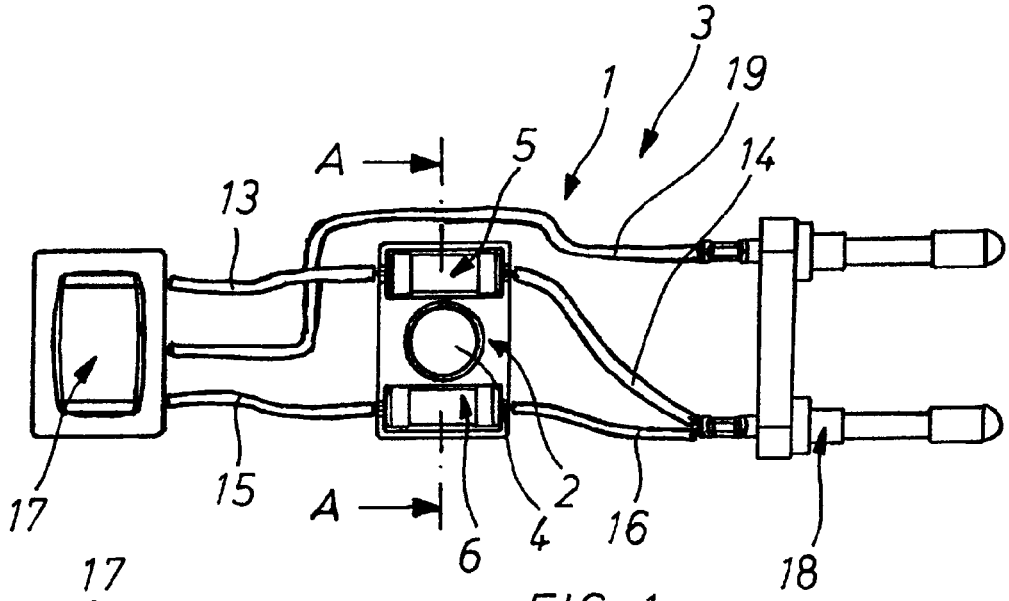
FIG. 1 shows a schematic top view of a heating device for the evaporation of volatile substances according to the invention.
Figure 2:
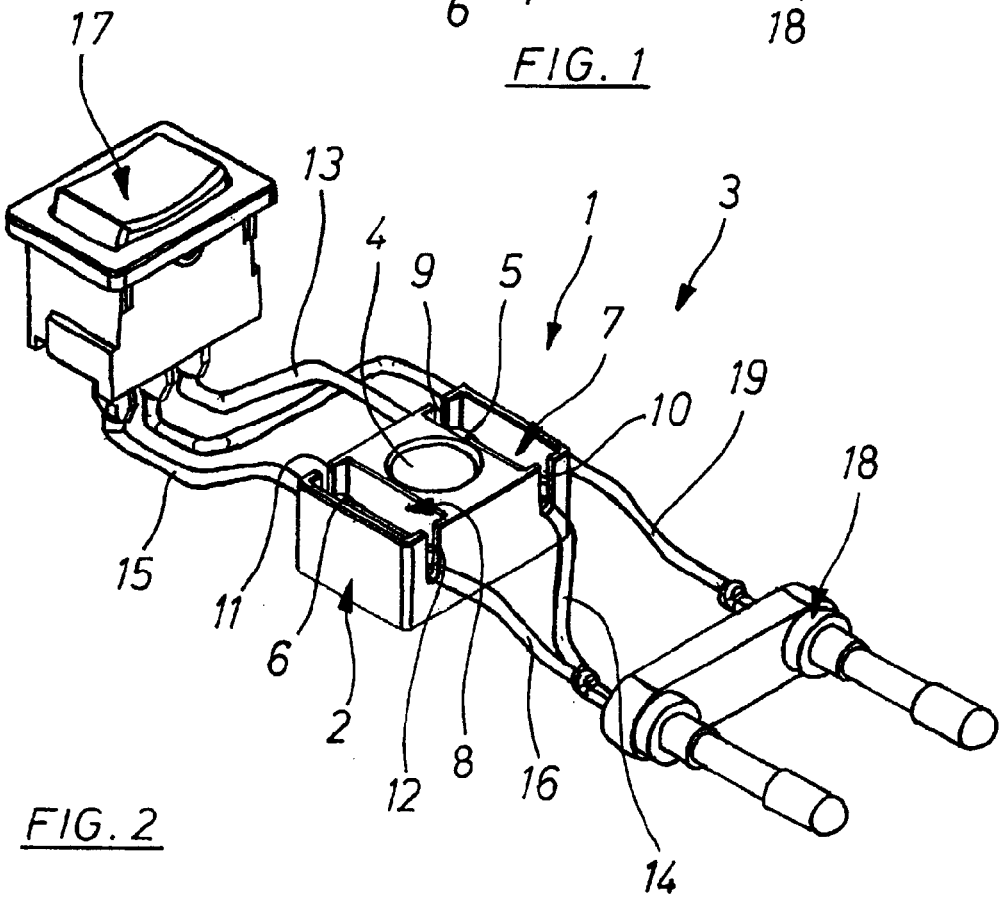
FIG. 2 shows a schematic perspective view of the device of FIG. 1.

FIGS. 1 and 2 show different schematic views of a heating device 1 with a heating block 2 as components of an evaporation device 3. Heating block 2 in the top plain view of FIG. 1 has an approximately rectangular form, with a wick opening 4 formed in an approximately central area of heating block 2. Wick opening 4 is approximately in the middle area between two heating elements in the form of electrical resistance heaters 5 and 6. As can best be seen in FIG. 2, heating elements 5 and 6 are located in openings 7 and 8 on heating block 2 and are encapsulated with highly heat-conductive material such as flame-resistant insulation is cement.

Figure 7:
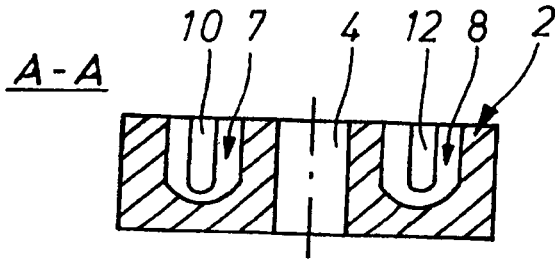
FIG. 7 shows a schematic sectional view along line A-A of FIG. 1.

On the opposite opening walls, on either side of heating elements 5 and 6, slits 9-12 are made through which electrical lines 13-16 connect to heating elements 5 and 6 and are routed. FIG. 7 shows a schematic cross-section through heating block 2 along line A-A of FIG. 1. Electric line 13 starts at heating element 5 and electric line 15 at heating element 6, each of which goes to manual switch 17, while electric line 14 of heating element 5 and electric line 16 of heating element 7, are respectively going to connection plug 18. Manual switch 17 is also connected via an electric line 19 to connection plug 18 to complete the circuit.

Figure 6:
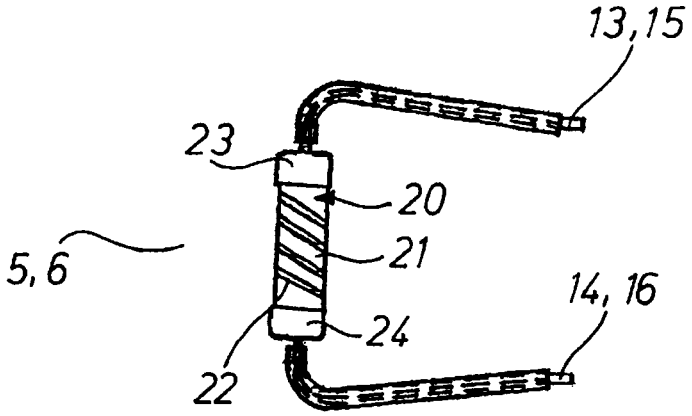
FIG. 6 shows a schematic top view of a resistance element for use in an evaporation device according to the invention.

FIG. 6 shows an enlarged view of the structure of heating elements 5 and 6. Thus, each of heating elements 5 and 6 comprise a rod-shaped resistance body 20 that is preferably made of a ceramic material with a certain content of $AL_2O_3$ for good heat conductivity. Resistance body 20 is coated with a metal oxide resistance layer 21. Resistance layer 21 is then laser cut so that a helicoidal cut 22 is formed around the rod-shaped cylindrical resistance body 20 to provide the adjustment of a given resistance value.

Metal caps, 23 and 24, are pressed on each end of the coated, rod-shaped cylindrical resistance body 20 for an electrical connection to resistance layer 21. To each of these caps, 23 and 24, one of electric lines 13-16, preferably made from copper wire, is welded and insulated with an insulation material. As can further be seen in FIG. 1, heating elements 5 and 6 are positioned approximately parallel to each other the same distance to wick opening 4 in the form of a passage opening. Preferably, heating elements 5 and 6 have different resistance values for different heating capacities.

Figure 5:
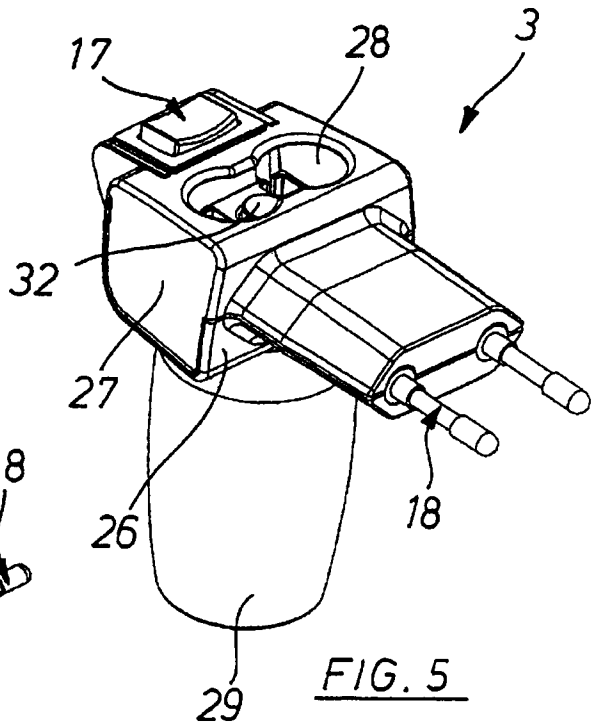
FIGS. 3-5 shows schematic representations of the assembly of the evaporation device in different stages of assembly according to the invention.
Figure 4:
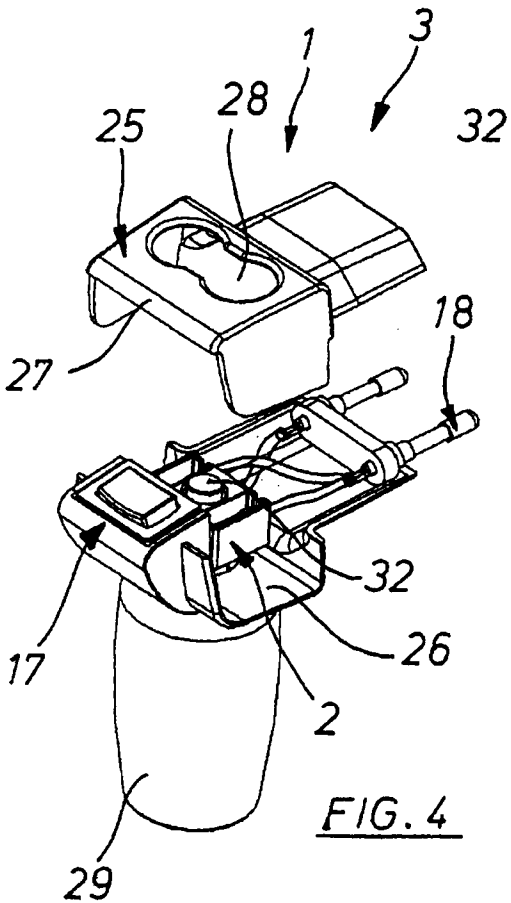
Figure 3:
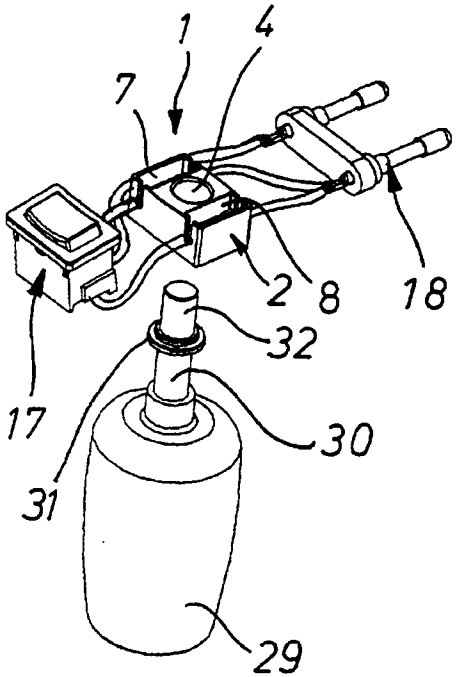

The assembly of the entire evaporation device 3 is explained step by step in FIGS. 3-5. As can best be seen in FIGS. 4 and 5, heating block 2 is received in an assembled state in housing 25. The heating block is connected to a lower shell 26 of the housing. Lower shell 26 contains a receptacle for the integration of manual switch 17 with housing 25. An upper shell 27 can be clipped on lower shell 26. Upper shell 27 is provided with an aeration slit 28 through which the substances to be evaporated can escape into the environment.

As best can be seen in FIGS. 3 and 4, a container 29, having a wick 30, is placed into housing 25 as an additional component of the evaporation device 3. Wick 30 can be fixed to container 29 by means of a wick holding ring 31 in such a manner that wick 30 has a wick end 32 protruding from within container 29. When container 29 is inserted into housing 25, wick end 32 extends into wick opening 4 of heating block 2, as can best be seen in FIG. 4. With an evaporation device 3 of this type, different operational states can be set. A first operational state can be set in which activation of manual switch 17 causes both heating elements 5 and 6 to be deactivated so that the heating block 2 is not heated. In the case where heating element 5 provides a greater heating capacity than heating element 6, by switching on heating 5 instead of 6, a rapid evaporation of the substances in the container to be evaporated takes place and is conveyed through the capillary action of wick 30 into the area of wick opening 4. If necessary, manual switch 17 can also be actuated in such manner that both heating elements 5 and 6 are switched on at the same time in order to achieve especially rapid and effective evaporation. The selection of the switch position, and thereby the selection of heating elements 5 and 6 for the evaporation of the volatile substances used, e.g., insecticides and/or aromatics, can be made a function of the evaporation capacity desired.

Figure 8:
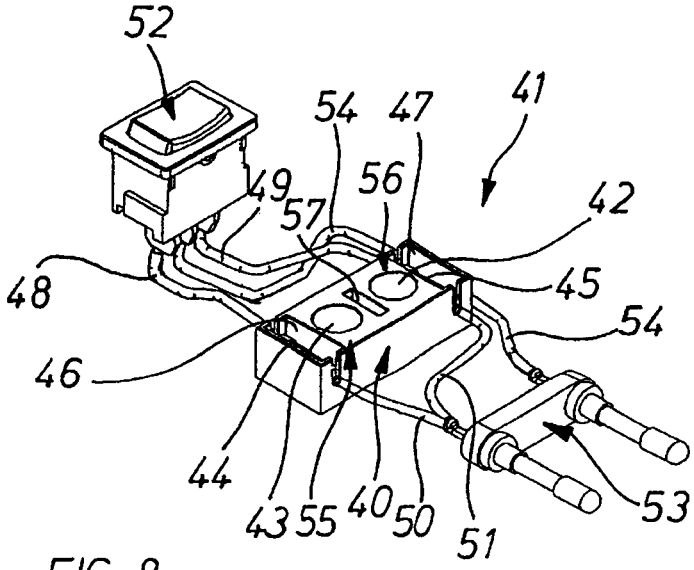
FIG. 8 shows a schematic perspective view of an alternative embodiment of a heating device for the evaporation of volatile substances according to the invention.
Figure 9:
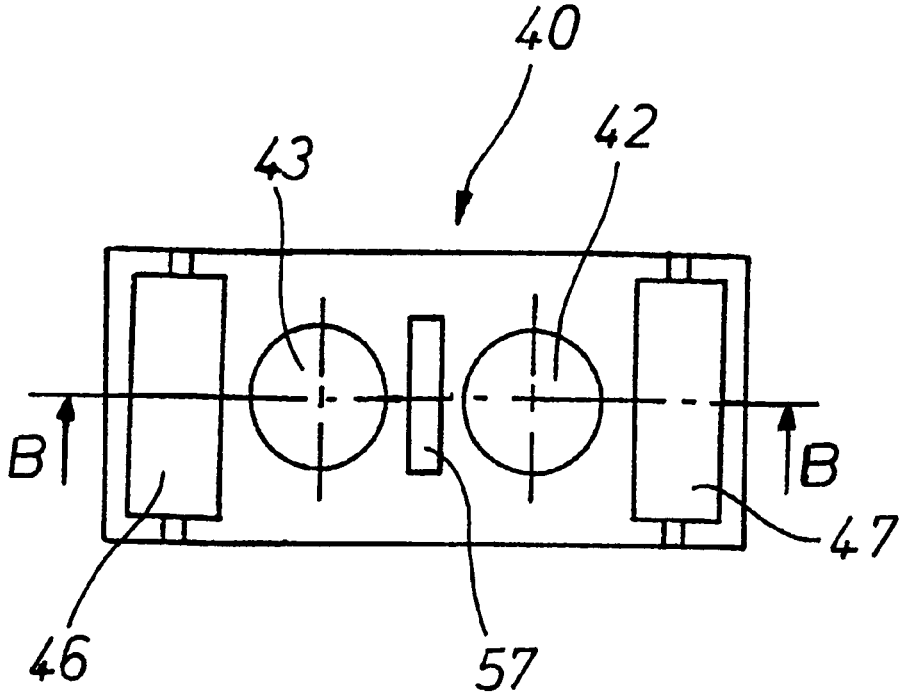
FIG. 9 shows a schematic top view of a heating block of the embodiment according to FIG. 8.
Figure 10:
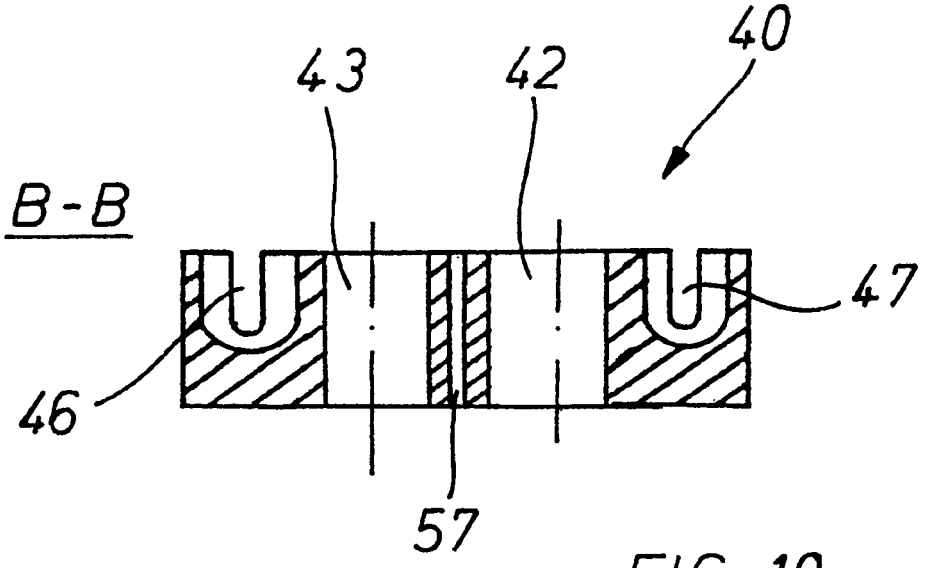
FIG. 10 shows a schematic sectional view along line B-B of FIG. 9.

FIG. 8 shows an alternative embodiment of a heating block 40 for an evaporation device 41, in which heating block 40 has two wick openings 42 and 43 at a distance from each other and located, as shown in the top plain view of FIG. 9, in a central area between two heating elements 44 and 45 at the edges of the heating block. FIG. 10 shows a cross-section along line B-B through heating block 40 of FIG. 9.

Heating elements 44 and 45 are designed as resistance element 3 described in detail with reference to FIGS. 1-7 and it is not necessary to discuss this in further detail. Preferably, heating elements 44 and 45 are capable of having different resistance values for adjusting the evaporation capacity.

Heating elements 44 and 45 are received in recesses 46 and 47 on heating block 40 and are cemented in place therein. Electrical connection lines 48-51 are assigned to each heating element 44 and 45. These electrical lines are routed through slits near the lateral recess walls in such a manner that connection line 48 of heating element 44, as well as connection line 49 of heating element 45, go to a manual switch 52. On the other hand, connection line 50 of heating element 44 and connection line 51 of heating element 45 go to a connection plug 53. In addition, an electric line 54 goes from manual switch 53 to connection plug 53.

FIGS. 8 and 10 further show an air gap 57 through heating block 40 as a separation between two wick recesses 42 and 43 to from an at least partial thermal uncoupling of two heating units 55 or 56. The heating units consisting of wick recess 42 and heating element 44, as well as wick recess 43 and heating element 45. Again, heating elements 44 and 55 preferably have different resistance values corresponding to the evaporation temperature adapted to the composition of the substance to be evaporated.

Figure 13:
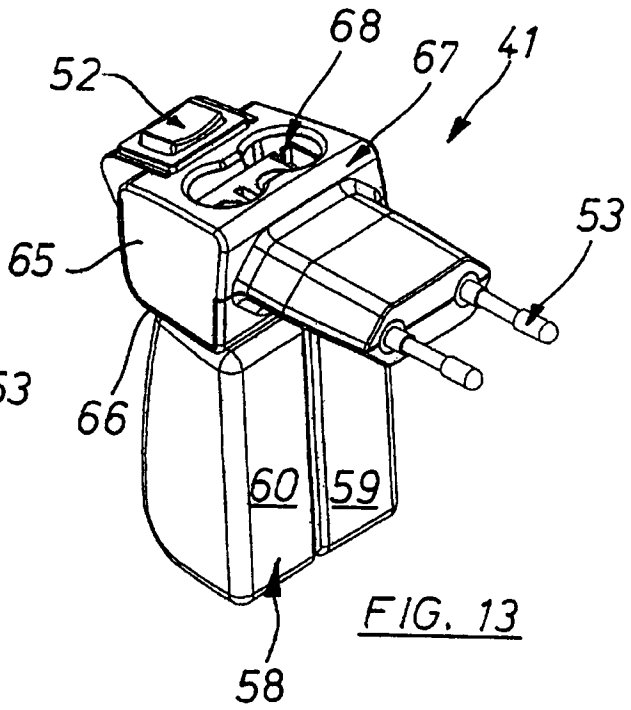
FIGS. 11-13 show schematic perspective views of the assembly of the device for the evaporation of volatile substances according to the alternative embodiment of FIG. 8 at different stages of assembly.
Figure 12:
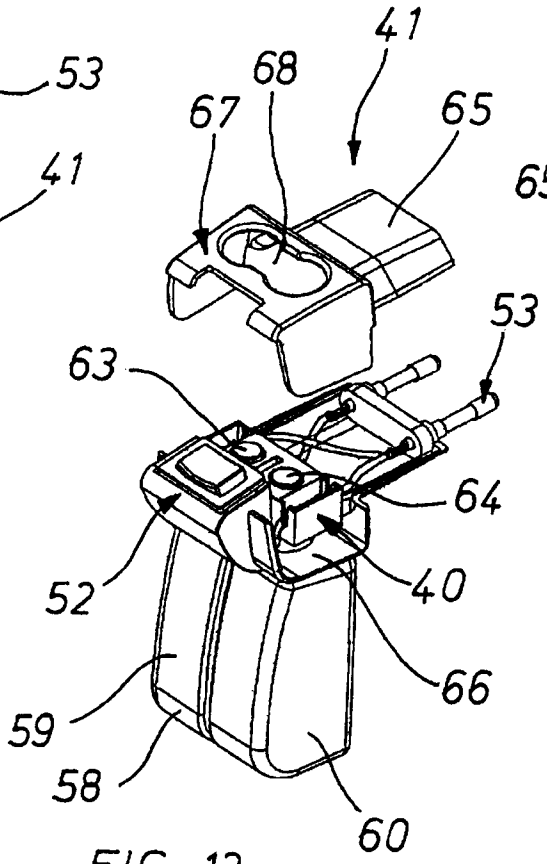
Figure 11:
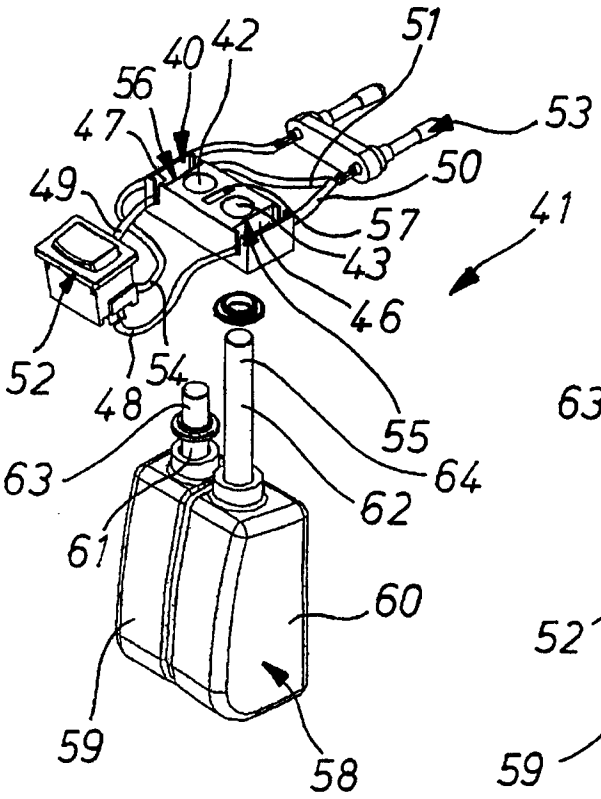

As can be seen in FIGS. 11-13, evaporation device 41 is also equipped with a container 58 having two chambers 59 and 60. Each chamber is assigned a wick 61 and 62 that, in the assembled state, extend with a wick end 63 and 64 from chamber 59 and 60. In the preferred embodiment, different substances to be evaporated with different evaporation temperatures are contained in chambers 59 and 60.

As can best be seen in FIG. 12, in the devices assembled state, heating block 40 is located in housing 67. Housing 67 consists of an upper housing shell 65 and a lower housing shell 66. A recess can be provided in housing 67 for the integration of manual switch 52. In addition, upper shell 65 is provided with an aeration slit 68. Heating units 55 and 56 can be activated separately via manual switch 52 so that either volatile substance contained in chamber 59 or 60 can be evaporated. The resistance value of heating elements 44 and 45 can be adapted to the substances in chambers 59 and 60 to be evaporated as described above. The manual switch can furthermore be provided with an additional switching position that activates both heating units 55 and 56 so that, especially in an aromatherapy, a mixture of aromatics can be produced by evaporation from both chambers 59 and 60. Alternatively, in another switching position of manual switch 52, heating units 55 and 56 can both be deactivated.

While a preferred embodiment of the invention has been described using specific terms, such description is for illustrative purposes only, and it is to be understood that changes and variations may be made without departing from the spirit or scope of the following claims.

What is claimed is:

[1. An evaporation device for evaporating volatile substances such as insecticides and aromatics comprising:

a housing containing a heating block with at least two heating elements having different heating capacities;

a container for a volatile substance to be evaporated;

a wick having a wick end protruding out of said container into a wick opening in said heating block;

a control device for the activation and deactivation of said heating elements; and said control device having a plurality of heat settings to vary the heat produced by the heating elements so the evaporation of the volatile substance may be controlled.]

[2. The device of claim 1 wherein said heating elements are operatively connected to said control device so that one or more of said heating elements may be selectively activated and deactivated to adjust the degree of evaporation.]

[3. The device of claim 1 wherein said heating elements are connected via electrical lines to a connection plug, and said control device is installed in said housing.]

[4. The device of claim 1 wherein said wick opening is formed in a central area of said heating block between two parallel aligned heating elements.]

[5. The device of claim 4 wherein said heating elements are spaced an equal distance from said wick opening so that a symmetric placement of said heating elements relative to said wick opening is achieved.]

[6. The device of claim 1 including at least one additional wick opening in said heating block assigned to at least one heating element; said additional wick opening being assigned to an additional container having a wick with a wick end extending into said additional wick opening for the evaporation of the substance contained in the additional container.]

[7. The device of claim 6 wherein said wick openings are spaced a distance from each other in a central area between said heating elements; said heating elements being disposed near the edge of said heating block.]

[8. The device of claim 6 including a single container having a first and second separate chamber, each chamber capable of containing a different substance to be evaporated, and said second chamber constitutes said additional container.]

[9. The device of claim 6 including at least one separator disposed in the area between said wick openings to achieve at least partial thermal uncoupling between wick openings and assigned heating elements.]

[10. The device of claim 9 wherein said separator includes an air gap extending through said heating block in the area between said wick openings.]

[11. The device of claim 1 wherein said heating elements comprise electrical resistance elements carried by said heating block.]

[12. The device of claim 11 wherein said resistance elements have different resistance values in order to make different heating capacities available for different volatile substances.]

[13. The device of claim 11 wherein said electrical resistance elements include rod-shaped, cylindrical resistance body to provide an overall miniaturized heating device for the evaporation of volatile substances; said rod-shaped resistance body being at least partially coated with a resistance layer to allow for the adjustment of a given resistance value corresponding to the evaporation temperature adapted to the composition of the substance to be evaporated; and said resistance layer being ground into said resistance body.]

[14. The device of claim 13 including a helicoidal spiral cut into said resistance lay of said rod-shaped, cylindrical resistance body to produce a given resistance value corresponding to the evaporation temperature adapted to the composition of the substance to be evaporated.]

[15. The device of claim 11 wherein said electrical resistance elements are encapsulated in said heating block by highly heat-conductive material; said heating block including openings through which electrical lines are passed to said connection plug and switching device.]

[16. The device of claim 1 wherein said control device includes one of a manual switch and a programmable microprocessor.]

[17. The device of claim 1 wherein said housing has an upper shell and a lower shell connected by locking elements; said lower shell having a connection member for connecting said container to said housing; and an aeration slit located above said wick ends so that evaporated volatile substance may escape.]

[18. An evaporation device for evaporating volatile substances such as insecticides and aromatics comprising:

a housing containing a heating block with a plurality of heating elements having different heating capacities;

a plurality of containers for a volatile substance to be evaporated;

a plurality of wick openings formed in said heating block;

a plurality of wicks having wick ends protruding out of said containers into said wick openings;

a control device for the activation and deactivation of said heating elements to adjust the heat produced by the heating elements and the evaporation of the volatile substance.]

[19. The device of claim 18 wherein said heating elements are operatively connected to said control device so that one or more of said heating elements may be selectively activated and deactivated to adjust the evaporation.]

[20. The device of claim 18 wherein said wick openings are formed in a central area of said heating block between two parallel aligned heating elements.]

[21. The device of claim 20 wherein said heating elements are spaced an equal distance from said wick opening so that a symmetric placement of said heating elements relative to said wick opening is achieved.]

[22. The device of claim 18 wherein said wick openings are spaced a distance from each other in a central area between said heating elements; said heating elements being disposed near the edge of said heating block.]

[23. The device of claim 18 including at least one separator disposed in the area between said wick openings to achieve at least partial thermal uncoupling between wick openings and assigned heating elements.]

[24. The device of claim 23 wherein said separator includes an air gap extending through said heating block in the area between said wick openings.]

[25. The device of claim 18 wherein said heating elements comprise electrical resistance elements having different resistance values in order to control the evaporation rate for different volatile substances.]

[26. The device of claim 25 wherein said electrical resistance elements include rod-shaped, cylindrical resistance body to provide an overall miniaturized heating device for the evaporation of volatile substances; said rod-shaped resistance body being at least partially coated with a resistance layer to allow for the adjustment of a given resistance value corresponding to the evaporation temperature adapted to the composition of the substance to be evaporated; and said resistance layer being ground into said resistance body.]

[27. The device of claim 26 including a helicoidal spiral cut into said resistance lay of said rod-shaped, cylindrical resistance body to produce a given resistance value corresponding to the evaporation temperature adapted to the composition of the substance to be evaporated.]

[28. The device of claim 18 wherein said control device includes one of a manual switch and a programmable microprocessor.]

*29. An evaporation device for evaporating volatile substances such as insecticides and aromatics comprising:*

*a housing;*

*a container for a volatile substance to be evaporated and carried in said housing;*

*a first wick carried in said container and having a first wick end protruding out of said container;*

*a heating block carried in said housing and having a first wick opening for receiving said first wick end;*

*a first heating element carried generally on a first side of said heating block and a second heating element carried generally on a second side of said heating block so that at least one of said heating elements heats said first wick end to effectively evaporate said volatile substance; and*

*a control switch for selectively activating and deactivating said heating elements to vary the heat output from the heating elements and control the evaporation rate for the evaporation of the volatile substance;*

*wherein said heating block further includes a second wick opening, said second wick opening being assigned to a second wick for evaporation of a second substance, said first heating element being associated with said first wick opening, and said second heating element being associated with said second wick opening and further wherein at least one separator is disposed in the area between said wick openings to achieve at least partial thermal uncoupling between wick openings and assigned heating elements.*

*30. The device of claim 29 wherein said control switch is manually operated, and said heating elements are operatively connected to said control switch so that one or more of said heating elements may be selectively activated to adjust the degree of evaporation.*

*31. The device of claim 29 wherein said heating elements are connected via electrical lines to a power connection plug via said control switch which is carried in said housing.*

*32. The device of claim 29 wherein the first and second wick openings are formed in a central area of said heating block and said heating elements are carried generally parallel on opposing sides of said heating block.*

*33. The device of claim 32 wherein the heating elements are spaced an equal distance from the respective wick openings so that a symmetric placement of said heating elements relative to said wick openings is achieved for uniform wick heating.*

*34. The device of claim 29 wherein said first and second wick openings are spaced a distance from each other in a central area between said heating elements; said heating elements being disposed between the edges of the heating block.*

*35. The device of claim 29 wherein the container includes a first and second separate chambers, each chamber capable of containing a different substance to be evaporated and said first and second chambers constitute first and second containers.*

*36. The device of claim 29 wherein said separator includes an air gap extending through said heating block in the area between said wick openings.*

*37. The device of claim 29 wherein said heating elements comprise electrical resistance elements carried by said heating block.*

*38. The device of claim 37 wherein said resistance elements have different resistance values in order to make different heating capacities available for different volatile substances.*

*39. The device of claim 37 wherein said electric resistance elements include rod-shaped, cylindrical resistance body to provide an overall miniaturized heating device for the evaporation of volatile substances; said rod-shaped resistance body being at least partially coated with a resistance layer to allow for the adjustment of a given resistance value corresponding to the evaporation temperature adapted to the composition of the substance to be evaporated; and said resistance layer being ground into said resistance body.*

*40. The device of claim 39 including a helicoidal spiral cut into said resistance layer of said rod-shaped, cylindrical resistance body to produce a given resistance value corresponding to the evaporation temperature adapted to the composition of the substance to be evaporated.*

*41. The device of claim 37 wherein said electrical resistance elements are encapsulated in said heating block by a highly heat-conductive material; said heating block including openings through which electrical lines are passed to said connection plug and switching device.*

*42. The device of claim 29 wherein said control device includes one of a manual switch and a programmable microprocessor.*

*43. The device of claim 29 wherein said housing has an upper shell and a lower shell connected by locking elements; said lower shell having a connection member for connecting*

*said container to said housing; and an aeration slit located above said wick ends so that evaporated volatile substance may escape.*

*44. An evaporation device for evaporating volatile substances such as insecticides and aromatics comprising:*

*a housing containing a heating block with at least two heating elements;*

*a container for a volatile substance to be evaporated;*

*a wick having a wick end protruding out of said container into a wick opening in said heating block;*

*a control device for the activation and deactivation of said heating elements, said control device having a plurality of heat settings to vary the heat produced by the heating elements so the evaporation of the volatile substance may be controlled;*

*at least one additional wick opening in said heating block assigned to at least one heating element, said additional wick opening being assigned to an additional container having a wick with a wick end extending into said additional wick opening, for the evaporation of the substance contained in the additional container; and*

*at least one separator disposed in an area between the wick openings to achieve at least partial thermal uncoupling between the wick openings and assigned heating elements.*

*45. The device of claim 44, wherein the separator includes an air gap disposed between the wick openings.*

*46. An evaporation device for evaporating volatile substances, comprising:*

*a housing containing a heating block having a plurality of heating elements;*

*a plurality of chambers each containing volatile substances to be evaporated;*

*a plurality of wick openings formed in the heating block wherein each heating elements is adjacent an associated one of the wick openings;*

*a plurality of wicks having wick ends protruding, out of the chambers into respective wick openings;*

*a control device to adjust the heat produced by the heating elements and the evaporation of the volatile substances; and*

*at least one separator disposed in an area between the wick openings to achieve at least partial thermal uncoupling between wick openings and respective heating elements;*

*wherein the heating elements are controlled to adjust evaporation from the chambers.*

*47. The device of claim 46 further including a control device that includes one of a manual switch and a programmable microprocessor.*

*48. The device of claim 47 wherein the control device includes a control switch that is operatively connected to said control switch so that one or more of said heating elements may be adjusted.*

*49. The device of claim 48 wherein said heating elements are connected via electrical lines to a power connection plug via said control switch which is carried in said housing.*

*50. The device of claim 46, wherein the separator includes an air gap disposed between the wick openings.*

*51. An evaporation device for evaporating volatile substances, comprising:*

*a housing containing a heating block with a plurality of heating elements and an air gap disposed between the first and second heating elements;*

*a plurality of containers containing volatile substances to be evaporated;*

*a plurality of wick openings formed in the heating block, wherein each heating element is adjacent an associated one of the wick openings;*

*a plurality of wicks having wick ends protruding out of the containers into the wick openings;*

*a control device to adjust the heat produced by the heating elements and the evaporation of the volatile substances; and*

*at least one separator disposed in an area between the wick openings to achieve at least partial thermal uncoupling between wick openings and respective heating elements;*

*wherein the heating elements are controlled to adjust evaporation from the containers.*

*52. The device of claim 51 further including a control device that includes one of a manual switch and a programmable microprocessor.*

*53. The device of claim 52 wherein said control device is a programmable microprocessor operatively connected to the heating elements so one or more of the heating elements may be selectively activated to adjust the degree of evaporation.*

*54. The device of claim 51 wherein the housing has an upper shell and a lower shell.*

* * * * *